US009981101B2

(12) United States Patent
VanMiddendorp et al.

(10) Patent No.: US 9,981,101 B2
(45) Date of Patent: May 29, 2018

(54) MEDICAL TUBE HOLDER AND RELATED METHODS

(71) Applicants: Grand Valley State University, Allendale, MI (US); Spectrum Health Innovations, LLC, Grand Rapids, MI (US)

(72) Inventors: Eric J. VanMiddendorp, Grand Rapids, MI (US); Timothy D. Stoepker, Grand Rapids, MI (US)

(73) Assignees: Sprectrum Health Innovations, LLC, Grand Rapids, MI (US); Grand Valley State University, Allendale, MI (US)

( * ) Notice: Subject to any disclaimer, the term of this patent is extended or adjusted under 35 U.S.C. 154(b) by 475 days.

(21) Appl. No.: 14/919,970

(22) Filed: Oct. 22, 2015

(65) Prior Publication Data
US 2016/0121067 A1 May 5, 2016

Related U.S. Application Data

(60) Provisional application No. 62/073,087, filed on Oct. 31, 2014.

(51) Int. Cl.
*A61M 16/04* (2006.01)
*A61M 16/08* (2006.01)
*A61M 16/06* (2006.01)

(52) U.S. Cl.
CPC .... *A61M 16/0488* (2013.01); *A61M 16/0816* (2013.01); *A61M 16/0875* (2013.01); *A61M 16/0683* (2013.01)

(58) Field of Classification Search
CPC ............ A61M 16/049; A61M 16/0493; A61M 16/0497; A61M 16/0488; A61M 25/02; A61M 2025/0206; A61M 2025/0253; A61M 2025/0266
See application file for complete search history.

(56) References Cited

U.S. PATENT DOCUMENTS

| 4,191,180 | A | * | 3/1980 | Colley | .............. | A61M 16/0488 |
|---|---|---|---|---|---|---|
| | | | | | | 128/207.17 |
| 5,353,787 | A | | 10/1994 | Price | | |
| 5,419,319 | A | * | 5/1995 | Werner | .............. | A61M 16/0488 |
| | | | | | | 128/200.26 |

(Continued)

*Primary Examiner* — Justine Yu
*Assistant Examiner* — Kathrynn Lyddane
(74) *Attorney, Agent, or Firm* — Warner Norcross + Judd LLP (57) ABSTRACT

A medical tubing holder system includes a connector, a holding assembly and a retainer block. The holding assembly has an arm, and optional flanges to capture part of medical tubing, such as an endotracheal tube. The retainer block is distal from the holding assembly. The retainer block defines an aperture that receives a tube therein. The aperture is smaller than a tube flange placed between the block and the holding assembly, so as to capture the tube flange. An attachment element joins the holding assembly to the retainer block, and has length that is adjustable to selectively vary a distance between the block and the holding assembly. The attachment element effectively secures the retainer block, holding the tube flange, to the holding assembly and connector, which is secured to the patient's head, to prevent self or accidental extubation. A related method is provided.

20 Claims, 7 Drawing Sheets

(56) References Cited

U.S. PATENT DOCUMENTS

| | | | |
|---|---|---|---|
| 5,782,236 A * | 7/1998 | Ess | A61M 25/02 |
| | | | 128/207.14 |
| 6,067,985 A | 5/2000 | Islava | |
| 6,526,978 B2 | 3/2003 | Dominguez | |
| 6,612,309 B1 | 9/2003 | Ancona | |
| 7,014,627 B2 | 3/2006 | Bierman | |
| 7,635,000 B2 | 12/2009 | Wilson et al. | |
| 8,740,852 B2 | 6/2014 | Aviles | |
| 2006/0118120 A1* | 6/2006 | Russo | A61M 16/0488 |
| | | | 128/207.14 |
| 2011/0214675 A1 | 9/2011 | Kost | |
| 2011/0240034 A1* | 10/2011 | Ciccone | A61M 16/0493 |
| | | | 128/207.17 |
| 2012/0103341 A1 | 5/2012 | Behlmaier | |
| 2012/0168571 A1* | 7/2012 | Bond | A61M 16/0488 |
| | | | 248/70 |
| 2013/0174844 A1 | 7/2013 | Doll et al. | |
| 2014/0261441 A1* | 9/2014 | Phillips | A61M 16/0497 |
| | | | 128/207.14 |
| 2014/0261462 A1* | 9/2014 | Visconti | A61M 16/0497 |
| | | | 128/861 |
| 2016/0271349 A1* | 9/2016 | Zickefoose | A61M 16/0497 |

\* cited by examiner

MEDICAL TUBE HOLDER AND RELATED METHODS

BACKGROUND OF THE INVENTION

The present invention relates to medical tube holders, and more particularly to an endotracheal tube holder that prevents self or accidental extubation.

There is a variety of medical tubing designed for different functions in relation to a patient. One type of medical tubing is an endotracheal tube (ETT). An ETT is configured to be inserted into a patient's oral cavity and a portion of their airway. The ETT is used to provide oxygen or other fluids to the patient. An issue with ETTs is that they may undergo unplanned extubation, or intentional self-extubation by the patient.

In an unplanned extubation, the ETT is removed accidentally, for example, during transport of the patient, while rolling the patient over, or via failure of an improperly supported ventilator tube. In self-extubation, a patient removes the ETT on their own, typically by grabbing and pulling the tube from their oral cavity, by thrashing from side to side or by pushing the tube out with their tongue. It has been discovered that there can be multiple adverse events following unplanned or self extubation, which can result in airway trauma, longer ventilation support durations, longer hospital stays and increased medical costs and increased health risks in general.

Many ETT supports that are suited to support the ETT, but do not prevent extubation well. Some of these supports include adhesive pads secured to the cheeks of the patient, with a frame secured to the pads to support the ETT in the patient's mouth. Many times, the adhesive pads cause issues because they do not adhere well, or migrate over time. There also are issues with many ETT supports causing pressure ulcers on the upper lip because they tend to push the ETT forcibly against it for long periods of time. Further, with some clamp-like supports, the clamps can become saturated with secretions, thus allowing the ETT to be easily pulled out.

Thus, there remains room for improving ETT supports so that they better support ETTs and address the issue of extubation.

SUMMARY OF THE INVENTION

A medical tube holder system adapted to prevent self or accidental extubation of a patient is provided. The medical tube holder can be an endotracheal tube (ETT) holder including a retaining block that selectively engages a flange of an ETT, where the retaining block is secured with adjustable length straps to a holding assembly.

In one embodiment, the system can include a connector, a holding assembly and a retainer block. The connector can extend across the patient's face, generally under their nose, and can be joined with the holding assembly. The holding assembly can optionally include an arm joined with flanges that cooperatively form a downwardly opening channel receiving part of an ETT or other tubing. The retainer block is distal and separate from the holding assembly.

In another embodiment, the retainer block can be in the form of a plate defining an aperture that receives the ETT therein. The aperture is smaller than an ETT flange, associated with the ETT. The ETT flange is placed between the retainer block and the holding assembly, so as to capture the flange and provide a mechanism to attach the flange to the connector, and ultimately to the patient's head more securely.

In still another embodiment, an attachment element joins the holding assembly to the retainer block. The attachment element can have a length that is adjustable to selectively vary a distance between the retainer block and the holding assembly. The attachment element effectively secures the retainer block, holding the ETT flange, to the holding assembly and connector, which is secured to the patient's head, to prevent self or accidental extubation.

In yet another embodiment, the attachment element includes a free end that extends through slots defined by the retainer block and/or holding assembly. By pulling on the free end, a user can selectively adjust the distance between the retainer block and the holding assembly, thus adjusting the overall orientation of the ETT relative to the patient's mouth, which can include the length of the exposed ETT. Optionally, the free end, or other portions of the attachment element can include a hook and loop fastener to fix the length of the strap.

In even another embodiment, the optional holding assembly flanges or arm, and wings of the retainer block, can define the slots for accommodating the attachment element, which can be in the form of a flexible strap. Optionally, the retainer block can be formed as a flat, thin plate with slots positioned on opposite sides of a plate axis, and adapted to receive corresponding attachment elements on opposite sides of the plate axis.

In a further embodiment, the system includes a pair of elongated face members that extend upwardly along the patient's cheeks, toward their temples. The elongated face members can be joined by another connector that extends at least partially across the patient's forehead. The elongated face members also can be secured rearward of the face with a strap that wraps around a rear of the patient's head.

In still a further embodiment, the elongated face members can be rigidly secured to the connector extending across the patient's face under the patient's nose. The connector can include a track configured to allow the holding assembly to be selectively placed multiple selected distances from a central plane of the patient's head.

In yet a further embodiment, a method is provided. The method can include positioning a connector under a patient's nose, extending a strap joined with the connector at least partially around at least one of the patient's neck and the patient's head to secure the connector to the patient's head, placing an arm of the holding assembly so that the arm extends forwardly, placing an ETT extending from the patient's mouth within a channel of the holding assembly, disposing a retainer block defining an aperture on an endotracheal tube connector so as to capture an ETT flange between the retainer block and holding assembly, securing an attachment element between the holding assembly and the retainer block, adjusting the length of the attachment element to selectively and/or precisely vary the distance between the retainer block and the holding assembly, and holding the retainer block a fixed distance from the holding assembly with the attachment element.

The current embodiments provide a tube holder system and method that prevent or impair self or accidental extubation. When a tube, such as an ETT, is pulled away under force from the patient's face or airway, the retainer block engages the flange on the tube. The pulling force can be transferred from the retainer block through the attachment element, to the holding assembly, and ultimately to the connector and strap to prevent the tube from being removed from the patient's oral cavity and/or airway. With this construction, the ETT is securely retained, and usually cannot be removed from the patient unless the entire holder system is removed. Where facial and head support structures are included, the system also is less prone to failure due to adhesive malfunctions. With the likelihood of self or accidental extubation reduced, it is expected that hospital stay durations, injuries, serious complications, high health care costs and other health risks associated with the same will likewise be reduced.

These and other objects, advantages, and features of the invention will be more fully understood and appreciated by reference to the description of the current embodiments and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENTS

I. Overview

A medical tube holder system adapted to prevent self or accidental extubation is illustrated in FIGS. 1-5 and generally designated 10. The system 10 can include a holding assembly 20, a retainer block 30 and one or more attachment elements 40A and 40B. These components are configured to selectively engage different portions of the endotracheal tube 100 when installed in a patient's mouth and/or airway.

Figure 1:
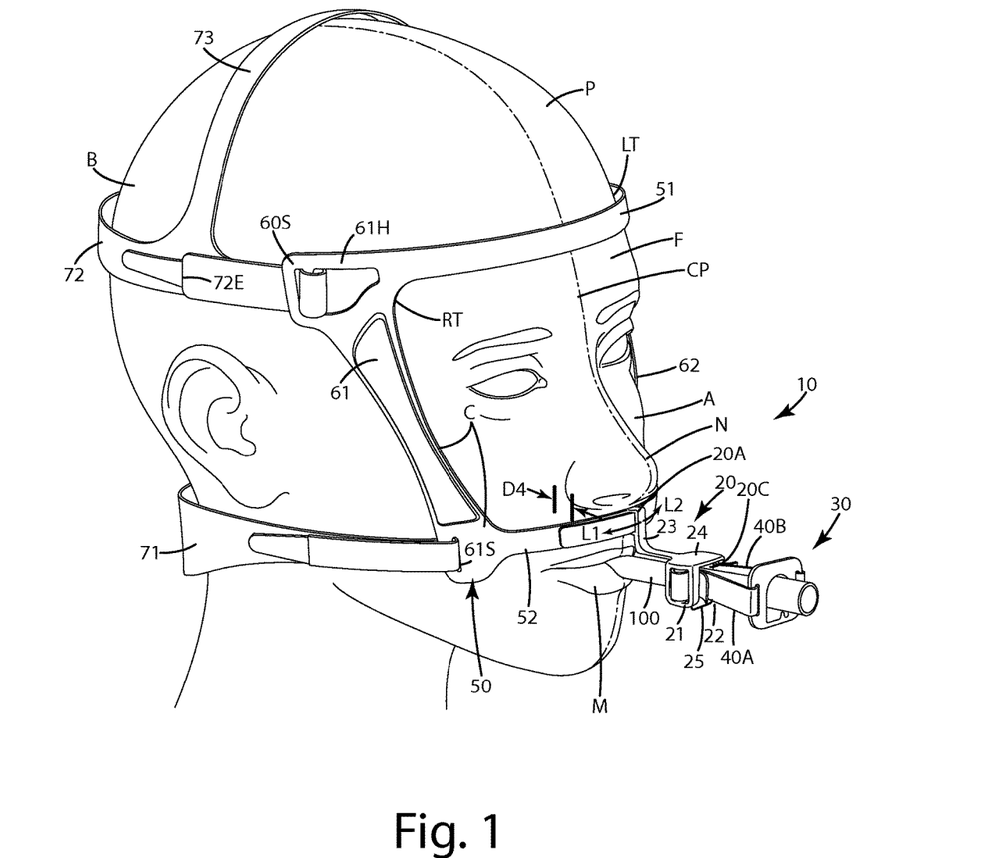
FIG. 1 is a perspective view of medical tube holder system installed on a patient.

The system 10 also can include a face support 50 having a curved or rounded track 52 which extends generally under the patient's nose, adjacent their upper lip. This track or connector 52 can be configured so that it extends outward a distance D4 away from the patient's skin above their lip. The distance D4 can be approximately 0.5 mm to about 10 mm or other distances depending on the particular application. Optionally, although the connector 52 may be placed away from the upper lip, it can be in contact with the lip. The connector generally runs parallel to the patient's upper lip, away from the patient's face. It also can be configured to allow adjustment of the holding assembly 20 laterally in directions L1 and/or L2 that extend on opposite sides of a central plane CP, which generally bisects the patient's head into left and right sides. With this connector construction, the incidence of pressure sores caused by the holding assembly can be reduced.

The face support 50 can include first 61 and second 62 elongate face members that extend from the second connector 52 to the first connector 51. The first connector 51 can extend laterally from temple RT to temple LT across the patient's forehead F. The first and second face members also can extend generally from the user's cheeks C to the user's respective right and left temples RT and LT on right and left sides L1 and L2 of the patient's P face. The face support 50 also can include a system of first and second straps 71 and 72 that extend around the anterior of the patient's neck and/or rear of their head for securement thereto.

Although described in connection with an ETT holder system that prevents extubation of a patient, wherein the all or a portion of the endotracheal tube ETT is withdrawn or pulled from the patient's airway and/or mouth M due to self or unplanned or accidental extubation, it will be appreciated that the tube holder system and methods of the current embodiments can be suited for use with other types of medical tubing. For example, the holder system and method can be used in connection with a nasal cannula or other tubing that is selectively disposed in orifices of the body.

Figure 3:
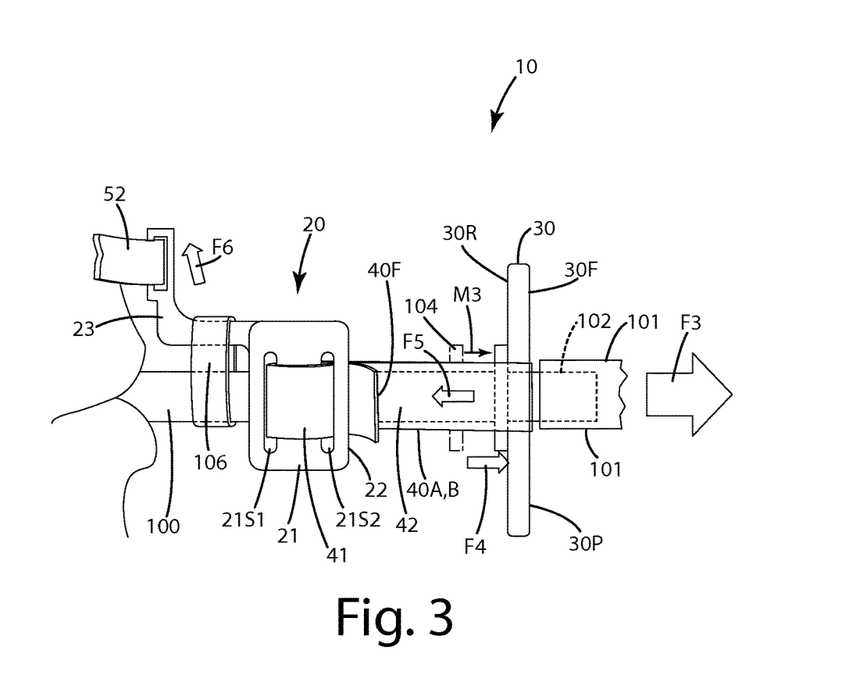
FIG. 3 is a side view of the medical tube holder system, and the application of a pulling force during a self or accidental extubation event.

In operation, the tube holder system can prevent or impair self or accidental extubation. For example, when an extubation force F3 is exerted upon a ventilation tube 101, which is further secured to an ETT connector 102 as shown in FIG. 3, the ETT flange 104 engages or further presses against a rear surface 30R of the retaining block 30 with a force F4, corresponding to the force F3. In some cases, the flange moves a distance M3 toward the retaining block. The actual movement M3 can be minuscule, but is greatly exaggerated in FIG. 3, and in some cases may not even evident to observers thereof. Indeed, sometimes, there may be no movement of the flange 104 upon application of the extubation force F3. In those cases, the flange 104 can be placed immediately adjacent and engaging the rear surface 30R of the retainer block 30.

The force F4 is transferred to the attachment elements 40A and 40B which in turn are joined with the holding assembly 20. The holding assembly 20 itself is joined or secured, for example, via adhesion with tape 106 or other fastening elements, to the ETT 100. The holding assembly 20 also is further attached with an arm 23 to the connector 52. This connector 52 is further joined with the face support 50. Thus, the extubation force F3 is transferred from the ventilator tube and/or ETT 100 to the flange 104, to the retainer block 30, through the attachment elements 40A, 40B, to the holding assembly 20, to the connector 52, and to one or more components of the face support 50 to effectively counter the extubation force and prevent an extubation event.

II. Construction

The different components of the tube holder system 10 will now be described in further detail with reference to FIGS. 1-5. As mentioned above, the construction optionally includes a face support 50 that is joined with a holding assembly 20, which is further attached via attachment elements 40A and 40B to a retainer block 30.

Starting with the optional face support 50 shown in FIG. 1, this construction can include a first connector 51 and a second connector 52. The first connector 51 can extend across the patient's forehead F crossing the central plane CP of the patient's head into left L2 and right L1 sides of the patient's face A. The second connector 52 can span across the patient's face crossing the central plane CP into left and right sides L1 and L2 of the face A. As mentioned above, the second connector 52 can be positioned between the nose N and the upper lip of the mouth M but can be disposed a preselected distance D4 away from the patient's upper lip to prevent ulcers, or optionally in contact with the lip. The second connector 52 can be curved and can follow the facial profile of the patient P, and optionally can include an adjustment mechanism 20A. This mechanism 20A can enable an arm 23 of the holding assembly 20 to move relative to the connector 52. When the connector is in the form of a track, such as that disclosed in U.S. Pat. No. 6,067,985 to Islava, which is hereby incorporated by reference in its entirety, this can enable the holding assembly 20 and ETT to be moved to the left L2 or right L1 of the central plane CP or aligned with it. This can be suitable when the patient is laying in different orientations and the ETT should exit the mouth M at different exit positions, or upon rotation of the ETT to prevent prolonged pressure in one area.

Optionally, the holding assembly also can include a bite block joined with or adjacent it. The bite block can be configured to protect the tube and prevent an intubated patient from biting through the tube. Further optionally, additional clips or hangers can be integrated into the face support and its components or straps in various locations to support other nearby tubes, such as nasogastric tubes and the like. Some other contemplated embodiments of the holding assembly are described farther below.

The second connector 52 is joined with the first face member 61 and second face member 62 at ends of the second connector. These components can be formed integrally as a single piece unit, optionally from a polymeric material. The polymeric material can be coated with rubber, fabric, gels or other types of materials that can reduce the friction and provide some cushion between the face structure and the patient's face A. Alternatively, a soft, nonabsorbent padding or cushion can be joined with the patient facing side of the face support components, connectors and/or straps to maximize comfort and minimize skin breakdown.

Optionally, the first connector 51 extending across the forehead F can be integral with and form a one piece structure with the first and second elongated face members 61 and 62 as well. Alternatively, the first connector can be an elastic strap that is joined at its ends with the elongated face members. Other constructions are contemplated.

The first and second elongated face members 61 and 62 can extend upwardly from cheek or jaw region C of the patient's face A, toward the respective right and left temples RT and LT. There, the elongated face members can be joined with the first connector 51, which again can span across the forehead F of the patient's face A. The elongated face members and/or connector can define one or more attachment holes 61H. These holes can be configured to receive one or more straps 72 that extend generally around the back of the wearer's head B. In some cases, these straps 72 can extend all the way around the forehead F as well, generally circumferentiating the patient's head, with the first connector 51 being deleted from the face support 50, and the strap 72 performing its supportive function.

Optionally, the strap 72 can be fitted through respective slots 60S adjacent the respective holes 61H with a strap free end 72E extending rearwardly along the side of the patient's head. The free end 72E can be pulled by a user to effectively tighten the strap 72 and connector 51 about the patient's head. Further optionally, a secondary strap 73 can be associated or joined with the strap 72 and can extend across the top of the patient's head to provide additional support to the other strap 72 and hold it in a fixed position.

As shown in FIG. 1, the optional face support 50 can include a lower or neck strap 71. This strap can be similar in structure to the strap 72 and can be looped through a slot 61S defined in the respective elongated face members 61, 62 and/or the end of the second connector 52. This strap 71 can secure the connector 52 to the patient's head in a relatively strong and robust manner so that the extubation force F3 transferred through the pulled upon ETT is ultimately transferred to the strap 71 and/or the face support 50 on the patient's head to prevent extubation.

Optionally, the straps 71, 72 and 73 can be constructed from a polymeric material which is flexible and configured to conform to the various contours of the patient's head. These straps also can be constructed from an elastic, nylon, fabric, weaved, knitted or other textile material that can be laundered easily and/or sterilized.

As mentioned above, the ETT 100 is generally configured to be placed inside the patient's mouth M and into the internal airways of the patient P. The ETT is of a tubular configuration, and includes a flange 104 and an ETT connector 102. Generally, the ETT connector 102 is of a larger diameter than the remainder of the ETT 100. This larger diameter can better correspond to ventilator or airway tubes 101 that are attached thereto. The flange 104 generally is of a larger diameter than the connector 102 as well as the remainder of the ETT 100. The flange usually operates as a stop to engage the end of the ventilator tube 101 and to properly install that tube on the connector 102 as illustrated in FIG. 3. In general, the holding assembly 20, retainer block 30 and attachment elements 40A, 40B take advantage of the structure of the ETT to assist in retaining the ETT and preventing self or accidental extubation. Optionally, the retainer block is configured to engage the ETT flange, preventing that from being pulled from the patient. Thus, in some cases, the airway tube 101 can be pulled off the connector 102, which renders the airway tube connection the natural failure point when the ETT is pulled away from the patient, instead of the ETT and connector. Thus, the ETT and connector can stay in place, even if the airway tube is removed or pulled out from the ETT connector.

Figure 2:
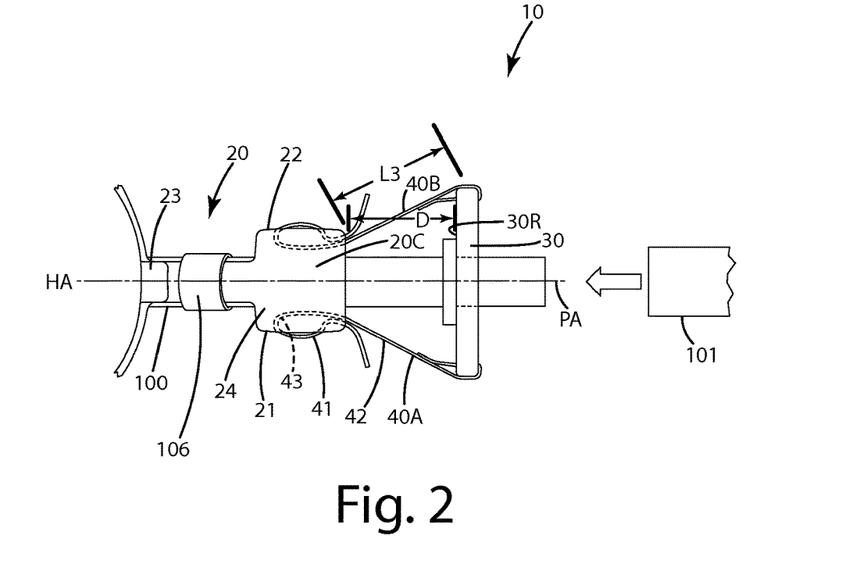
FIG. 2 is a top view of the medical tube holder system.

As shown in FIGS. 2 and 3, one type of holding assembly 20 includes an arm 23 that extends downwardly and is optionally movably attached and lockable relative to the second connector 52 of the facial structure 50. The arm 23 transitions to a holder plate 24 that can be a larger width or dimension than the arm 23 itself. The holder plate 24 is joined with first 21 and second 22 flanges that extend generally downwardly from the plate 24. These flanges can be parallel, and can cooperate to form a downwardly opening channel 20C. The flanges 21 and 22 can extend downwardly optionally about 1 mm to about 25 mm, further optionally about 5 mm to about 20 mm depending on the particular application and the size of the ETT. The flanges can form a C- or U-shaped channel as mentioned above. The channel optionally includes an open side 25 so that the ETT 100 can be inserted from the underside of the holding assembly, up and into the channel 20C where it is retained in use.

Figure 4:
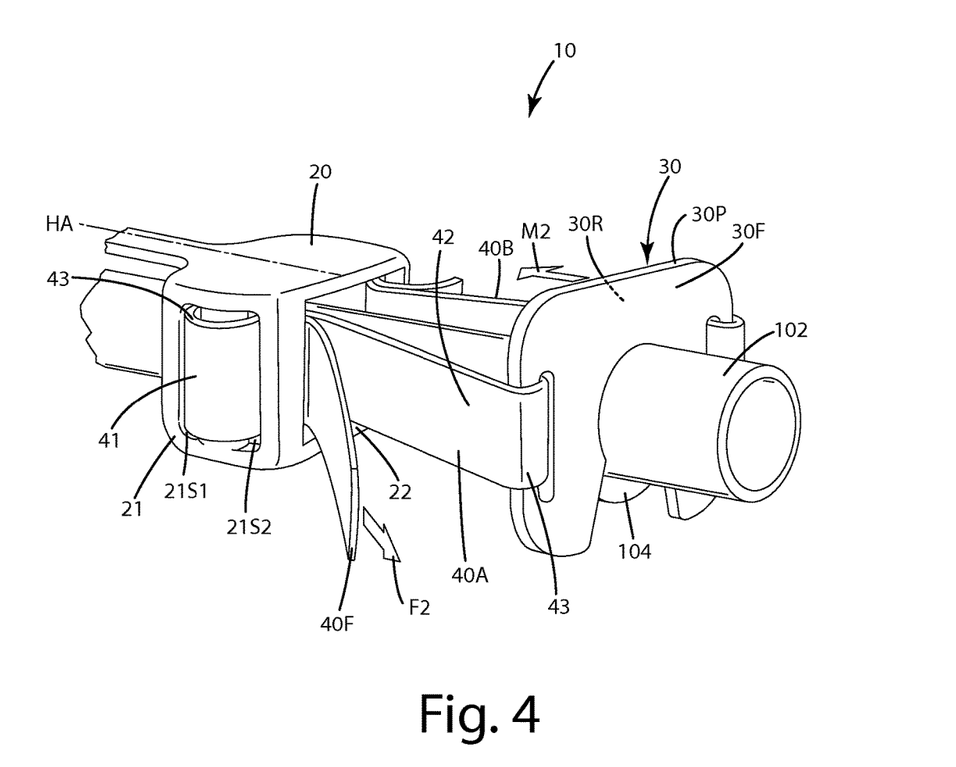
FIG. 4 is a perspective view of one type of holding assembly joined with a retainer block utilizing an attachment element.

The first 21 and second 22 flanges can define first and second slots 21S1 and 21S2 as shown in FIGS. 3 and 4. There, the slots are generally elongated and configured to receive at least a portion of the attachment elements. These slots can be similar in structure and function to the slots 31S and 32S as described in connection with the retainer block 30 below. The slots can be spaced from one another so that the attachment element can be threaded through the same and frictionally engage the edges of the slots and/or portions of the holding assembly or flanges to secure the attachment elements thereto.

Optionally, the holding assembly 20 can include a holder axis HA. The first flange 21 can be disposed on a first side of the holder axis HA, while the second flange 22 can be disposed on opposite side thereof. Likewise both of the respective slots 21S1 and 21S2 as well as the slots on the opposing flange 22 can be disposed on opposite sides of the holder axis HA. Further optionally, the holding assembly and its components may or may not be symmetric about the holder axis HA.

The holding assembly 20 can be configured so that the arm and/or plate can be secured fixedly to the ETT 100 with an anchoring element 106 as shown in FIGS. 2 and 3. This anchoring element 106 as illustrated can be in the form of medical tape having an adhesive side and an exterior side. The adhesive side can include an adhesive that adheres to the arm 20 and the exterior surfaces of the ETT 100 with which it contacts. The anchoring element can be wrapped sufficiently around the arm and/or holding assembly, along with the ETT, to fixedly secure the holding assembly in a single fixed location relative to the ETT. The precise location can depend on the depth of the insertion of the ETT in the patient's airway or other factors. With the anchoring element, the holding assembly 20 also is secured to the ETT to prevent the ETT from being pushed farther into the patient's mouth M. Although the anchoring element is shown as a piece of adhesive tape, this tape can be replaced with a clamp, zip tie, tie down or fastener to secure the ETT in fixed relation relative to the holding assembly 20.

Optionally, the anchoring element can be in the form of an integrated strap that extends from the holding assembly (not shown). The strap can include an adhesive backing to retain the endotracheal tube when wrapped there around. In particular, the strap can extend through a slot in the holding assembly and wrap around the tube. The strap can define a hole in the wrapped around end. A bulb or hook can be integrated into the holding assembly. The hole in the strap can slip over the bulb to secure the free end of the strap in place, thereby adhesively and physically securing the tube in place. This strap can be slightly elastic to accommodate any size tube and also provide some clamping force.

As shown in FIGS. 2 and 3, the holding assembly 20 is spaced a distance D from the retaining block 30. The distance D can be preselected depending on the desired insertion and depth at which the ETT is placed in the patient. The retaining block 30 can be configured as a plate, having a relatively flat featureless front 30F and rear 30R surfaces. These surfaces can be bounded by a perimeter 30P. This perimeter can extend generally around the substantial portion of the retainer block 30.

Figure 5:
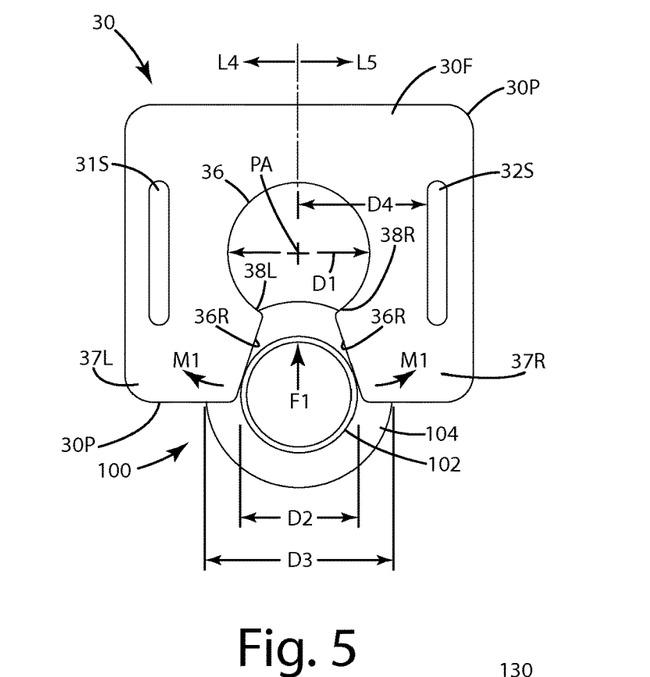
FIG. 5 is a top view of the retainer block being installed on a medical tube connector, adjacent a flange of the medical tube.

The retainer block 30 as shown in FIGS. 3-5 can define an aperture 36. This aperture 36 can be centered on or disposed near the central plate axis PA of the plate which generally bisects the plate into left L4 and right L5 sides that can be of equal dimension. The aperture 36 can be sized slightly larger than the ETT connector 102. For example, the inside dimension or diameter D1 as shown in FIG. 5 of the aperture 36 can be slightly larger than the dimension or diameter D2 of the connector 102. The dimension of the aperture 36 can also be smaller than the dimension or diameter D3 of the ETT flange 104. In this manner, the flange 104 and tube 100 cannot be pulled through the aperture 36 without deforming and/or destroying the retainer block 30.

As shown in FIG. 5, the retainer block 30 can include first and second ramps 36R. The ramps 36R can be angled or rounded portions that merge into the perimeter 30P of the retainer block 30, as well as the aperture 36. The ramps 36R can be configured so that when the ETT connector 102 is forced with a force F1 into the retainer block toward the aperture 36 and/or toward the plate axis PA of the retainer block 30, that force F1 engages the ETT connector 102 against the ramps 36R. Accordingly, the retainer block deforms slightly so that the left and right side portions 37L and 37R of the retainer block 30 moves in directions M1, generally away from the axis PA until the connector element 102 is fully disposed within the main portion of the aperture 36. At this point, the side portions 37L and 37R move in directions opposite of M1, and secure the connector 102 within the aperture 36. The protrusions 38L and 38R can engage a portion of the connector 102 to hold it in place. In some cases the ETT connector 102 "snaps" into the aperture 36 creating an audible snap or click. This construction is referred to as a "snap fit" construction.

Optionally, the retainer block, holding assembly and/or face support can be constructed of polymeric materials such as polypropylene, high density polyethylene, polyurethane, nylon, composites, metals or other constructions depending on the particular application and environment.

The retainer block 30 can define first and second slots 31S and 32S that are disposed opposite one another across the axis PA of the retainer block 30. Generally, these slots are defined on the left L4 and right L5 sides of the retainer block 30. The slots can be elongated, and can be parallel if desired. It is also contemplated that slots as used herein encompasses recesses, apertures, holes or other like voids defined by the retainer block. The precise shape and configuration and depth of these slots 31S, 32S can vary depending on the attachment elements and their proposed function. Optionally, the slots can be positioned at a distance D4 from the plate axis, which distance D4 can be greater than or equal to half the dimension D1 (0.5 D1) of the aperture 36.

As mentioned above, the aperture 36 can be configured to be smaller than the dimension of the ETT flange 104. Thus, the ETT flange typically abuts the rear surface 30R of the retainer block or plate 30 as shown in FIG. 3. The retainer block 30 also can be disposed between the flange 104 and the ventilator tube 102 as described above.

Figure 6:
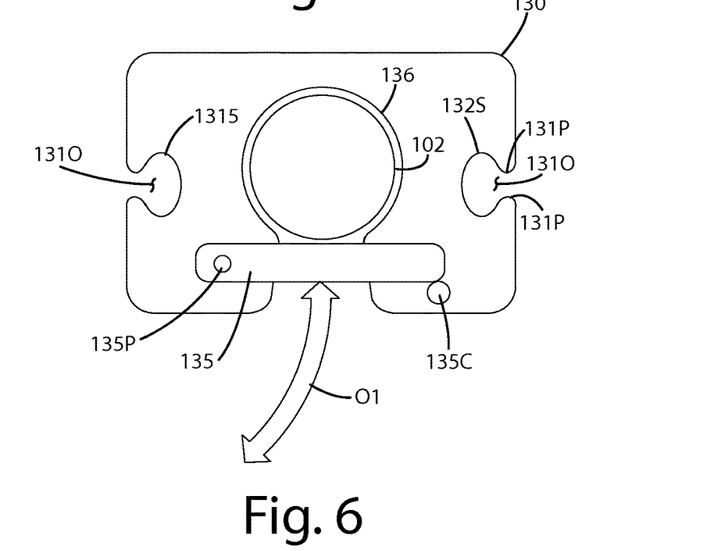
FIG. 6 is a first alternative embodiment of the tube holder system including another retainer block.

A first alternative embodiment of the retainer block is shown in FIG. 6 and generally designated 130. This retainer block 130 can include an aperture 136 configured to receive the ETT connector 102. The retainer block 130, however, can be constructed to include a moveable or swinging latch 135 that pivots about a pivot axis 135P. This latch 135 can be locked in position as shown in FIG. 6 via a catch 135C, which generally holds the latch 135 against the bottom of the ETT connector 102. The latch 135 can be opened in the direction O1 so that the ETT connector 102 can be installed and/or removed from the retainer block 130.

In this first alternative embodiment of the tube holder system, a retainer block 130 includes retainer block slots 131S and 132S that can be slightly different from that of the embodiment shown in FIG. 5. For example, these slots 131S and 132S each can include an opening 131O that opens directly to the environment rather than being a closed off slot. These slots, however, can include projections 131P that can assist in at least partially capturing an attachment element when placed there through.

Figure 8:
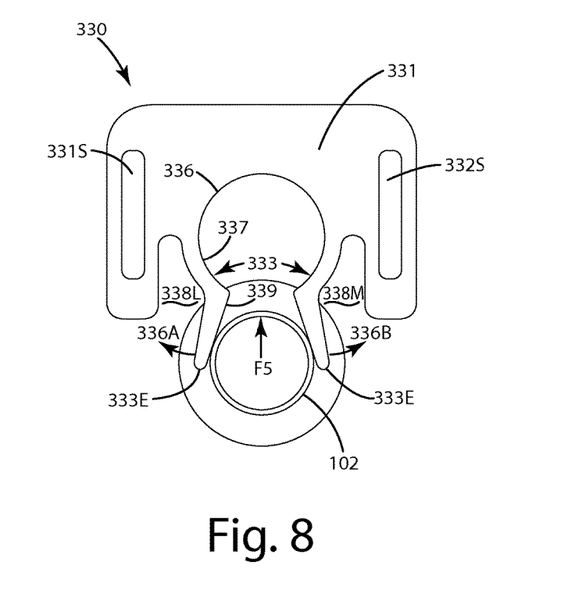
FIG. 8 is a third alternative embodiment of the tube holder system including even another retainer block.

A third alternative embodiment of the tube holder system including another retainer block is shown in FIG. 8. This retainer block 330 can include an aperture 336 configured to receive the ETT connector 102. The retainer block 330, however, can be constructed to include first and second resilient arms or fingers 333. These arms can extend from a main body 331 of the retainer block 330 and can include free distal ends 333E. Each arm 333 can include a first portion 337 which is attached to the main body 331, and a distal second portion 339, which generally includes the free distal end 333E. The first portion 337 can be configured to trap and hold the connector 102. Optionally the first portion can be of a circular, elliptical and/or rounded shape. The first portion 337 transitions to the second portion 339, which includes a slanted or tilted ramp on the interior thereof. The ramp includes an interior surface that engages the connector 102 when it is inserted with force F5 toward the aperture 336. The second portions 339 of the arms 333 and/or the first portions 337 can bend or flex in directions 336A and 336B. This can occur when the connector 102 is inserted toward the aperture 336. In turn, the arms 333 resiliently or dynamically flex or bend toward and/or into the openings 338L and 338M on the opposing sides of the arms 333. These openings allow outward movement of the arms so that the connector 102 can be inserted into the aperture 336, passing by the ramps of the second portion 339.

Returning to the current embodiments shown in FIGS. 1-5, the tube holder system also can include one or more attachment elements 40A and 40B. These attachment elements can be in the form of flexible or non-rigid elements, for example, straps. The straps can be constructed from a flexible plastic ribbon, textile material, fabric, polymer, laminate or other structure. Generally, portions of the attachment element 40A and 40B can include hook-and-loop fasteners so that the attachment elements can be folded over upon themselves and secured in place, at a fixed, preselected length.

The attachment elements 40A and 40B can be constructed to include a free end 40F. This free end can be joined with a holding assembly portion 41 that is threaded through the slots 21S1 and 21S2 of the holding assembly 20. That portion 41 can be further joined with or transition to a connecting portion 42 that extends generally from the holding assembly toward the retaining block 30. That connecting portion can be joined with a second end 43 that is threaded through or otherwise joined with the respective slots 31S and 32S of the retaining block 30. The holding assembly portion 41 again can be threaded through the slots 21S and 21S2. Optionally, the end 40F of the attachment element also can be disposed between the holding assembly and the retainer block upon installation of the same.

Operation of the attachment elements can include pulling on the free end 40F. In so doing, the length L3 of the attachment element between the holding assembly 20 and the retaining block 30 can be adjusted. In turn, the overall distance D between the forward portion of the holding assembly 20 and the rear face 30R of the retaining block can be adjusted in length to custom fit the ETT and the holder system to the patient. As the force F2 is applied, pulling on the free end 40F, the holding assembly portion 41 of the attachment element slides through the respective slots 21S1 and 21S2. This in turn pulls the main portion 42 toward the holding assembly 21. This further pulls the retainer block 30 in direction M2 generally decreasing the distance D between the retaining block 30 and the holding assembly 20. When the force F2 is reversed, that is, when the end 40F is pushed toward or through the slots 21S2 and 21S1, the retaining block 30 moves in opposite direction from M2, thereby increasing the distance D between the retaining block and the holding assembly. In this case, the ETT can move slightly out from the airway of the patient P. Optionally, the lengths of the attachment elements 40A and 40B can be equal so that the retainer block 30 is generally squared relative to the front surface of the holding assembly 20.

Figure 7:
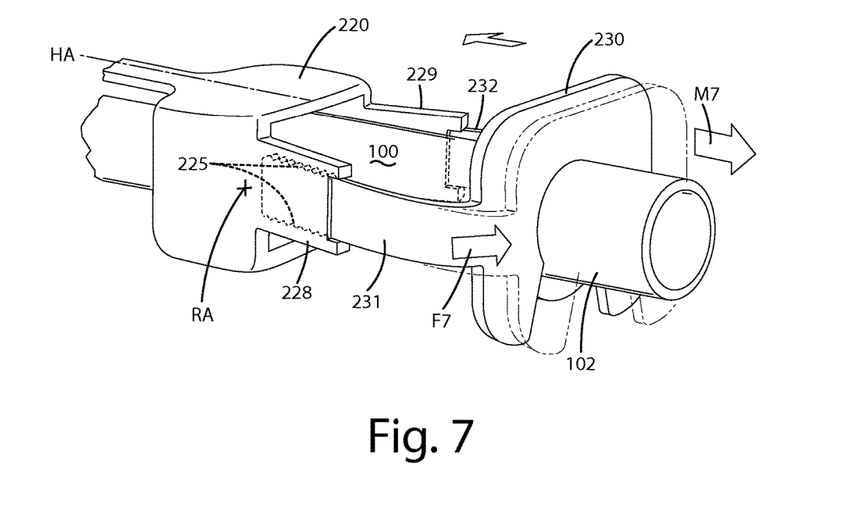
FIG. 7 is a second alternative embodiment of the tube holder system including yet another retainer block, associated attachment elements and holding assembly.

A second alternative embodiment of the tube holder system is illustrated in FIG. 7 and generally designated 210. There, the retainer block 230 includes legs 231 and 232 that extend rearwardly toward the holding assembly 220. The legs 231 and 232 can be integrally formed with the retainer block rather than as separate straps in the embodiment above. The legs 230 can be telescopingly disposed within sleeves 228 and 229 disposed on opposing sides of a holder axis HA. The sleeves 228 and 229 can receive the respective legs 231 and 232. The legs 230 can telescope relative to the sleeves 228 and 229 so that the retainer block 230 can be set a preselected from the holding assembly 220. The legs and sleeves also can be configured so that the retaining block can generally pivot about a pivoting axis RA so as to be able to move and be installed on different portions of the ETT 100.

Optionally, the legs and/or sleeves can include a locking mechanism 225. As illustrated, this can be a toothed mechanism which can selectively lock the legs 231 in fixed orientation and alternatively enable the legs to extend or retract relative to the sleeves 228 and 229. In this manner, the distance between the retainer block and the holding assembly 220 can be fixed or selectively altered. Upon actuation of the locking mechanism 225, and application of a force F7 by a user, the retaining block 230 can be moved in direction M7, depending on the desired modification and set up of the retainer block 230 relative to the holding assembly 220. Other constructions are contemplated for the respective attachment elements and retaining block.

Figure 9:
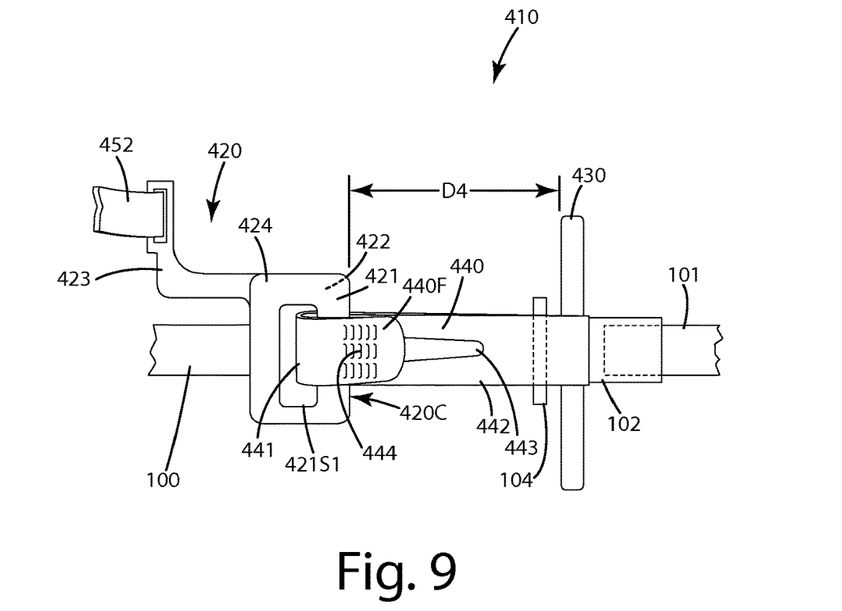
FIG. 9 is a fourth alternative embodiment of the tube holder system including another holding assembly.

A fourth alternative embodiment of the tube holder system is illustrated in FIG. 9 and generally designated 410. This embodiment can be similar to the embodiments described above in structure, function and operation, with a few exceptions. For example, the holding assembly and attachment elements in this embodiment can be slightly different. The holding assembly 420 can include a forwardly extending arm 423 that is connected to a connector 452. This connector can be in the form of a strap that extends around the rear of the patient's head. The holding assembly arm 423 can extend forward to a plate 424, which can be a larger width or dimension than the arm 423 itself. The holder plate 424 can be joined with first 421 and second 422 flanges that extend generally downwardly from the plate 424. These flanges can be parallel, and can cooperate to form a downwardly opening channel 420C. The flanges can form a C- or U-shaped channel to receive the ETT tube as mentioned in the embodiments above. The first 421 and second 422 flanges can each define a single slot 421S1. The single slot can be elongated and configured to receive at least a portion of the attachment elements.

The attachment elements 440 can be similar to the attachment elements in the embodiments above with slight modifications. For example, the attachment elements 440 can be constructed to include a connecting portion 442 that extends generally from the holding assembly to the retaining block. The connecting portion 442 can be joined with a holding assembly portion 441 that is threaded through the single slot 421S1 on each flange of the holding assembly 420. That portion 441 can be further joined with or transition to an end 440F. The end 440F can be constructed to include a fastening element 444 that attaches to a corresponding fastening element on the connecting portion 442. As an example, the fastening element can be in the form of hook and loop fasteners. The connecting portion 442 can include corresponding hook and loop fasteners, or alternatively can be constructed from a material that attaches easily to the hook and loop type fasteners. Optionally, the fastening element can be in the form of an adhesive, button, hook, or some other fastening structure so that the end 440F can be secured to the connecting portion 442, thereby attaching the attachment element 442 to the holding assembly 420. Further optionally, the end 440F of the attachment element also can be disposed between the holding assembly and the retainer block upon installation of the same. In this embodiment, the retainer block can be similar in structure and function to that of the embodiments above.

As shown in FIG. 9, the holding assembly 420 can be spaced a distance D4 from the retaining block 430. The distance D4 can be preselected depending on the desired insertion and depth at which the ETT is placed in the patient. The distance D4 also can be modified by attaching the end 440F at different portions along the connecting portion 442 of the attachment element 440, optionally utilizing the fastening elements 444. Further optionally, the and 440F can include a grasping tab 443 that enables a user to easily grasp and remove the end and/or attach the end 440F to respective parts on the connecting portion 442.

Figure 10:
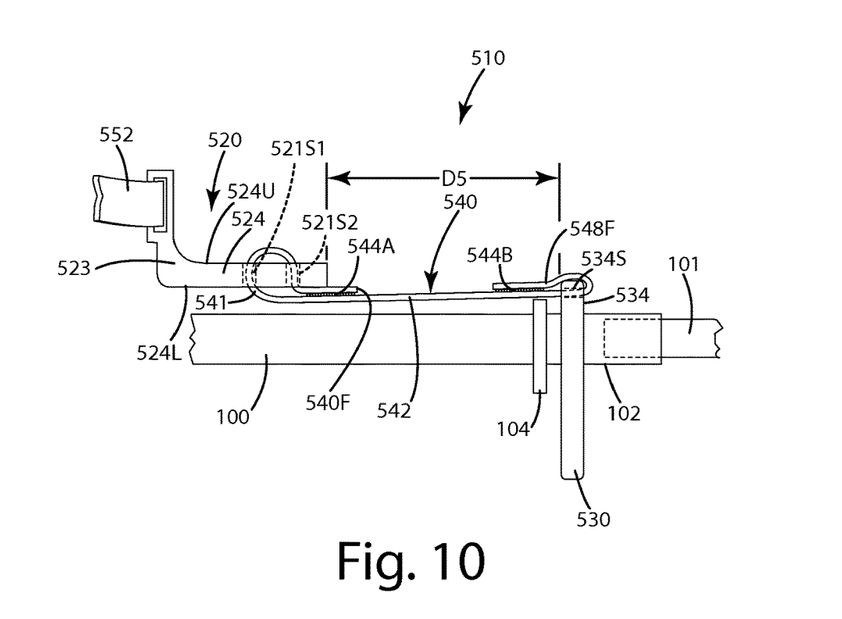
FIG. 10 is a fifth alternative embodiment of the tube holder system including yet another holding assembly.

A fifth alternative embodiment of the tube holder system is illustrated in FIG. 10 and generally designated 510. This embodiment can be similar to the embodiments described above in structure, function and operation, with a few exceptions. For example, the holding assembly and attachment elements in this embodiment can be slightly different. The holding assembly 520 can include a forwardly extending arm 523 that is connected to a connector 552. This connector can be in the form of a strap that extends around the rear of the patient's head. The holding assembly arm 523 can extend forward to an extended portion that can be in the form of a plate 524. Optionally, this plate includes no downwardly extending flange ease or wings. Instead, the plate 524 itself can define one or more slots 521S1 and 521S2 that extend through the plate, from an upper surface to a lower surface. The slots can be elongated from side to side, across the width of the plate. The slots can accommodate a holding assembly portion 541 of the attachment element 540. The holding assembly portion 541 can be snaked through the slots as illustrated.

Optionally, the holding assembly portion 541 can initially extend below the lower surface 524L of the plate 524, through the rearward most slot 521S1, above the upper surface 524U of the plate 524, then back down through the forward slot 521S2. The attachment element 540 can include an end 540F. The end 540F can include one or more fasting elements 544A that attach the end and secure it generally to the connecting portion 542 of the attachment element 540. The fasting elements 544A can be hook and loop fasteners, buttons, hooks, adhesives or other types of elements that can generally fasten the end 540F to the connecting portion 542 to assist in fixing the distance D5 between the holding assembly 520 and the retainer block 530.

In this embodiment, the attachment element 540 can be a single attachment element extending above the ETT 100, rather than two attachment elements disposed on opposite sides thereof as in the above embodiments above. Accordingly, the attachment element 540 can attach primarily to an upper portion 534 of the retainer block 530. In particular, it can extend through a slot 534S defined in the upper portion 534. The connecting portion 540 can extend to a second end 548F. The second end can be folded back upon the connecting portion 542 of the attachment element 540. The end 548F can include one or more fastening elements 544B, which can be similar to the other fasting elements 544A noted above. Accordingly, the end 548F can be secured to the connecting portion to assist in fixing the distance D5 between the holding assembly and retainer block. Optionally, other than the slot 534S being mounted in the upper portion of the retaining block, that retaining block can be similar to the other embodiments of retaining blocks described herein.

Figure 11:
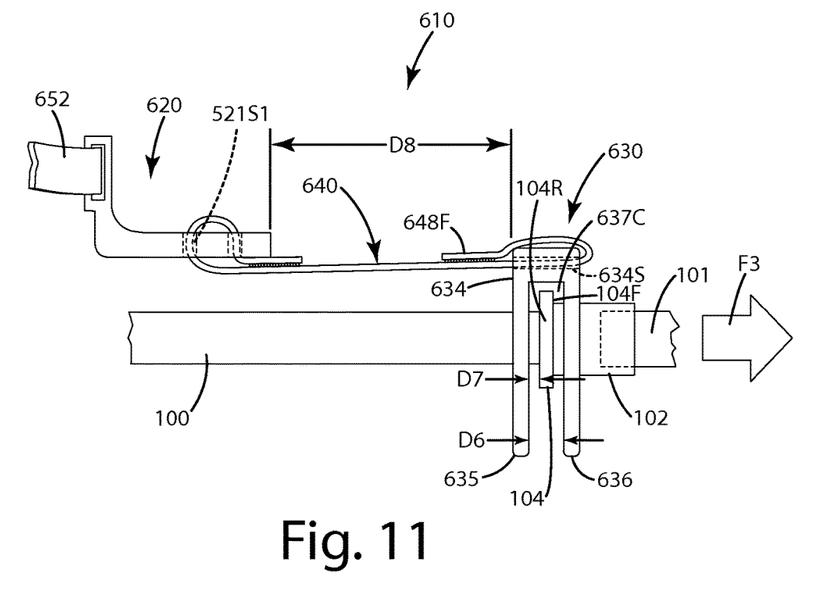
FIG. 11 is a sixth alternative embodiment of the tube holder system including another holding assembly and another retainer block.

A sixth alternative embodiment of the tube holder system is illustrated in FIG. 11 and generally designated 610. This embodiment can be similar to the embodiments described above in structure, function and operation, with a few exceptions. For example, the retainer block in this embodiment can be slightly different. The holding assembly 620 can be similar to that of the embodiment shown in FIG. 10, and can include an attachment element 640 that extends to and is joined with an upper portion 634 of the retainer block 630. In the embodiment of FIG. 10, there is the potential for unwanted tipping of the retainer block 530 as a force is applied to the airway tubing 101.

To mitigate this translation and tipping, which can unnecessarily kink or bend the ETT 100, the retainer block 630 shown in FIG. 11 can include forward 636 and rearward 635 plates or sections. These plates or sections can be similar to the retainer block constructions shown in FIGS. 5, 6 and 8 of the other embodiments, with the exception of having a slot 634S in the upper portion 634 of the retainer block. Optionally, the rearward plate 635 also can include a simple C or U-shaped slot within which the ETT tube 100 fits, but might not include special ramps or retaining features if desired.

The forward and rearward plates also can be spaced a distance D6 from one another. This distance D6 is sufficient to enable the ETT flange 104 to fit between the plates 635 and 636. This distance D6 can be optionally 2 mm-8 mm, further optionally 2 mm-6 mm. Generally, the distance D7 between the ETT flange and either of the respective plates can be optionally less than 3 mm and further optionally less than 1 mm. The plates can be structured and placed so that if a force F3 is applied to the tubing 101, the forward and rearward plates 636 and 635 prevent excessive tipping of the retainer block because those plates are effectively trapping or securing the front and rear surfaces 104F, 104R of the ETT flange.

III. Methods of Use

A method of using the endotracheal tube holder system of the current embodiment will now be described in connection with FIGS. 1-5. Generally, an ETT tube 100 is inserted into a patient's P airway. The face support 50 is installed upon the patient's P head. The first connector 51 is installed across the forehead and the second connector is installed across the upper lip. The first and second elongated face members 61 and 62 join with the connectors 51 and 52. The respective straps 71 and 72 are placed at least partially around at least one of the patient's neck and the patient's head to secure the connectors to the patient's head.

With the face support installed, the holding assembly 20 generally projects forwardly of patient's face and mouth M. The arm 20 and respective holding assembly 20 are moved to the left L2 and/or right L1 of the center plane CP of the patient's head depending on the desired exit location of the ETT from the mouth M. For example, the holding assembly can be moved to a corner of the mouth, near the central plane CP, or other locations therebetween.

The holding assembly, joined with the connector, is placed so that the arm 23 of the holding assembly 20 extends forwardly from the patient's mouth M. The ETT 100 is inserted through the open side 25 so it enters the downwardly opening channel 20C. The flanges 21 and 22 as well as the plate 24 are disposed adjacent and can abut the ETT 100 when placed in the downwardly opening channel of the holding assembly 20. The holding assembly 20 is fixedly joined with the endotracheal tube ETT with the anchoring element 106. Where in the form of tape, the anchoring element is wrapped around the arm 23 and a portion of the ETT adjacent that arm. With the anchoring element installed, the holding assembly 20 is secured to the ETT to prevent the ETT from being pushed farther into the patient's mouth M.

As shown in FIGS. 2-5, the retainer block 30 is pushed downwardly over the connector 102 adjacent the flange 104 of the ETT. This moves the sides 37R and 37L of the retaining block 30 in directions M1 as shown in FIG. 5 until the connector 102 is secured within the aperture 36. The attachment elements are threaded through the respective slots of the retaining block and holding assembly. As shown in FIG. 4, the free end 40F of the attachment element 40A can be pulled with a force F2. This moves the attachment element through the respective slots 21S1 and 21S2, thereby pulling the retaining block 30 in direction M2 until a desired orientation of the holding assembly and/or depth of the ETT 100 within the patient's airway is achieved.

After installation of the holder system, when the ETT 100 is pulled away from a patient's face, for example, with the extubation force F3 as shown in FIG. 3, the ETT flange 104 engages the retaining bock 30. This transmits corresponding force F4 to the retaining block, and then to the attachment elements to the retaining block 30. That force is transferred via force F5 through the attachment elements 40A, 40B to the holding assembly 20. Ultimately, this force F6 is transmitted to the connecter and to the other portions of the face support 50. The force is further transferred to the respective straps associated with the face support and absorbed to prevent and/or impair extubation or pulling of the ETT from the patient's mouth and/or airway.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z ; and Y, Z.

The embodiments of the invention in which an exclusive property or privilege is claimed are defined as follows:

1. An endotracheal tube holder system comprising:
a connector joined with at least one strap that extends at least partially around at least one of the patient's neck and the patient's head to secure the connector to the patient's head;
a holding assembly joined with the connector, the holding assembly having an arm that is adapted to extend forwardly away from the patient's face, the holding assembly having a first flange and a second flange;
a retainer block defining an aperture adapted to receive an endotracheal tube connector therein, the aperture being of a first dimension that is greater than a second dimension of the endotracheal tube connector, the first dimension being less than a third dimension of an endotracheal tube flange of an endotracheal tube;
an attachment element extending from at least one of the first flange and the second flange of the holding assembly to the retainer block, the attachment element having a first length, the first length being adjustable to selectively vary a distance between the retainer block and the holding assembly;
wherein the attachment element holds the retainer block a fixed distance from the holding assembly,
whereby when the endotracheal tube is pulled away under an extubation force from the patient's face, the retainer block restrains the endotracheal tube connector from being moved away from the patient's face, with the extubation force being transferred through the attachment element, to the holding assembly, and ultimately to the connector and strap to prevent the endotracheal tube from being removed from the patient.

2. The endotracheal tube holder system of claim 1,
wherein the holding assembly includes an attachment area adapted to receive an anchoring element that fixedly joins the holding assembly to the endotracheal tube,
wherein the attachment area is formed on the arm,
wherein the anchoring element is an adhesive tape wrapped around the arm and the endotracheal tube, adhering to both.

3. The endotracheal tube holder system of claim 2,
wherein the first and second flanges form a downwardly opening U-shaped channel,
wherein the channel only partially circumferentiates the endotracheal tube when the endotracheal tube is placed therein.

4. The endotracheal tube holder system of claim 3,
wherein the attachment element is a flexible attachment strap including a first end, a second end, and a middle portion therebetween,
wherein the first end is joined with the retainer block,
wherein the middle portion engages at least one of the first flange and the second flange,
wherein the second end is freely graspable by a user,
whereby a user can reduce the first length by pulling the second end away from the holding assembly.

5. The endotracheal tube holder system of claim 4 wherein the middle portion folds over upon itself.

6. The endotracheal tube holder system of claim 1,
wherein the first and second flanges of the holding assembly cooperatively form a channel adapted to receive a first portion of an endotracheal tube therein,
wherein the holding assembly includes an attachment area adapted to receive an anchoring element that fixedly joins the holding assembly to the endotracheal tube,
wherein the holder assembly includes a holder axis,
wherein the first flange defines a first flange slot on a first side of the holder axis,
wherein the retainer block defines a first retainer block slot,
wherein the attachment element extends through the first flange slot and the first retainer slot, with a first free end of the attachment element located between the holding assembly and the retainer block.

7. The endotracheal tube holder system of claim 6,
wherein the second flange defines a second flange slot on a second side of the holder axis, opposite the first side of the holder axis,
wherein the retainer block defines a second retainer block slot.

8. The endotracheal tube holder system of claim 1 comprising:
a first elongated face member adapted to extend from a patient's cheek, upward toward a patient's temple, the first elongated face member adapted for being disposed on a left side of the patient's face; and
a second elongated face member adapted to extend from the patient's cheek, upward toward a patient's temple, the second elongated face member adapted for being disposed on a right side of the patient's face,
wherein the connector is disposed between and joins the first elongated face member and the second elongated face member.

9. The endotracheal tube holder system of claim 8 comprising:
another connector disposed between and joining the first elongated face member and the second elongated face member, the other connector adapted for positioning across at least a portion of the patient's forehead; and
another strap joined with the first elongated face member and the second elongated face member, the strap adapted for being disposed around at least one of a rear of a patient's head and a patient's neck.

10. An endotracheal tube holder system comprising:
a first elongated face member constructed from a polymeric material, the first face member adapted to extend from a patient's cheek, upward toward the patient's temple, the first elongated face member adapted for disposal on a left side of the patient's face;
a second elongated face member constructed from the polymeric material, the second elongated face member adapted to extend from the patient's cheek, upward toward the patient's temple, the second elongated face member adapted for disposal on a right side of the patient's face;
a first connector disposed between and joining the first elongated face member and the second elongated face member, the first connector adapted for positioning across at least a portion of a patient's forehead;
a second connector disposed between and joining the first elongated face member and the second elongated member, the second connector distal from the first connector and adapted for positioning under a patient's nose;
at least one strap joined with the first elongated face member and the second elongated face member, the at least one strap adapted for being disposed around at least one of a rear of a patient's head and a patient's neck;
a holding assembly joined with the second connector, the holding assembly having an arm that is adapted to extend forwardly away from the patient's face, the holding assembly including first and second downwardly extending flanges that cooperatively form a channel adapted to receive a first portion of an endotracheal tube therein, the holding assembly including an adhesion area adapted to receive an adhesive tape to fixedly join the holding assembly to a preselected location along the endotracheal tube, the first downwardly extending flange defining a first flange slot, the second downwardly extending flange defining a second flange slot;
a retainer block in the form of a plate including a perimeter, the retainer block defining an aperture, the aperture including a plate axis, the plate configured to selectively deform so that the aperture enlarges when an endotracheal tube connector is inserted into the aperture in a direction toward the plate axis, the aperture being of a first dimension that is greater than a second dimension of the endotracheal tube connector, the first dimension being less than a third dimension of an endotracheal tube flange of the endotracheal tube, the plate defining a first plate slot on a first lateral side of the plate axis and a second plate slot on a second lateral side of the plate axis;
a first flexible attachment element extending from the holding assembly to the plate, through the first flange slot and the first plate slot, the first flexible attachment element having a first length, the first length being adjustable to selectively vary a first distance between the first flange and the plate;
a second flexible attachment element extending from the holding assembly to the plate, through the second flange slot and the second plate slot, the second flexible attachment element having a second length, the second length being adjustable to selectively vary a second distance between the first flange and the plate; and a track associated with the second connector so that the holding assembly and endotracheal tube can be selectively, laterally moved relative to a central plane of the patient's head.

11. The endotracheal tube holder system of claim 10 wherein the first flexible attachment element and the second flexible attachment element are each in the form of elongated straps, each elongated strap including a hook and loop fastener.

12. The endotracheal tube holder system of claim 10,
wherein the first flange defines a third flange slot,
wherein the second flange defines a fourth flange slot,
wherein the first flexible attachment element extends through the first flange slot and the third flange slot,
wherein the second flexible attachment element extends through the second flange slot and the fourth flange slot.

13. The endotracheal tube holder system of claim 10,
wherein the first flange defines a third flange slot that is parallel to the first flange slot,
wherein the second flange defines a fourth flange slot that is parallel to the second flange slot.

14. The endotracheal tube holder system of claim 10,
wherein the arm is adapted to support the holding assembly forward of a patient's mouth so that the holding assembly is adapted to support the endotracheal tube extending into the patient's mouth.

15. The endotracheal tube holder system of claim 10,
wherein the first connector is constructed from the polymeric material,
wherein the first elongated face member, the second elongated face member and the first connector are integrally formed with one another as a one-piece structure.

16. The endotracheal tube holder system of claim 10 wherein the plate includes first and second ramps extending toward an outer perimeter of the aperture.

17. The endotracheal tube holder system of claim 10 wherein the plate includes a first side portion and a second side portion extending laterally away from the plane axis on opposite sides of the aperture, therein the first and second side portions define the first and second plate slots, respectively.

18. A method of using an endotracheal tube holder comprising steps of:
positioning a connector under a patient's nose,
extending a strap joined with the connector at least partially around at least one of the patient's neck and the patient's head to secure the connector to the patient's head;
placing a holding assembly, joined with the connector, so that an arm of the holding assembly extends forwardly away from the patient's mouth, wherein the holding assembly comprises a channel;
placing an endotracheal tube extending from the patient's mouth within the channel;
joining the holding assembly to the endotracheal tube with an anchoring element;
disposing a retainer block defining an aperture on an endotracheal tube connector, the aperture being of a first dimension that is greater than a second dimension of the endotracheal tube connector, the first dimension being less than a third dimension of an endotracheal tube flange of the endotracheal tube;
securing an attachment element to the holding assembly and to the retainer block;
adjusting a first length of the attachment element to selectively vary a distance between the retainer block and the holding assembly; and
holding the retainer block a fixed distance from the holding assembly with the attachment element,
whereby when the endotracheal tube is pulled away under an extubation force from the patient's face, the retainer block restrains the endotracheal tube connector from being moved away from the patient's face, with the extubation force being transferred through the attachment element, to the holding assembly, and ultimately to the connector and strap to prevent the endotracheal tube from being removed from the patient.

19. The method of claim 18 wherein the anchoring element is adhesive tape, the method comprising a step of taping the holding assembly to the endotracheal tube.

20. The method of claim 18 comprising a step of pulling on an end of the attachment element to draw the retainer block closer to the holding assembly.

\* \* \* \* \*

UNITED STATES PATENT AND TRADEMARK OFFICE
CERTIFICATE OF CORRECTION

PATENT NO.       : 9,981,101 B2  
APPLICATION NO.  : 14/919970  
DATED            : May 29, 2018  
INVENTOR(S)      : Eric J. VanMiddendorp et al.

Page 1 of 1

It is certified that error appears in the above-identified patent and that said Letters Patent is hereby corrected as shown below:

On the Title Page

(73) Assignees: "Sprectrum Health Innovations, LLC" should be --Spectrum Health Innovations, LLC--

Signed and Sealed this
Twenty-first Day of August, 2018

Andrei Iancu
*Director of the United States Patent and Trademark Office*